Figure 1:
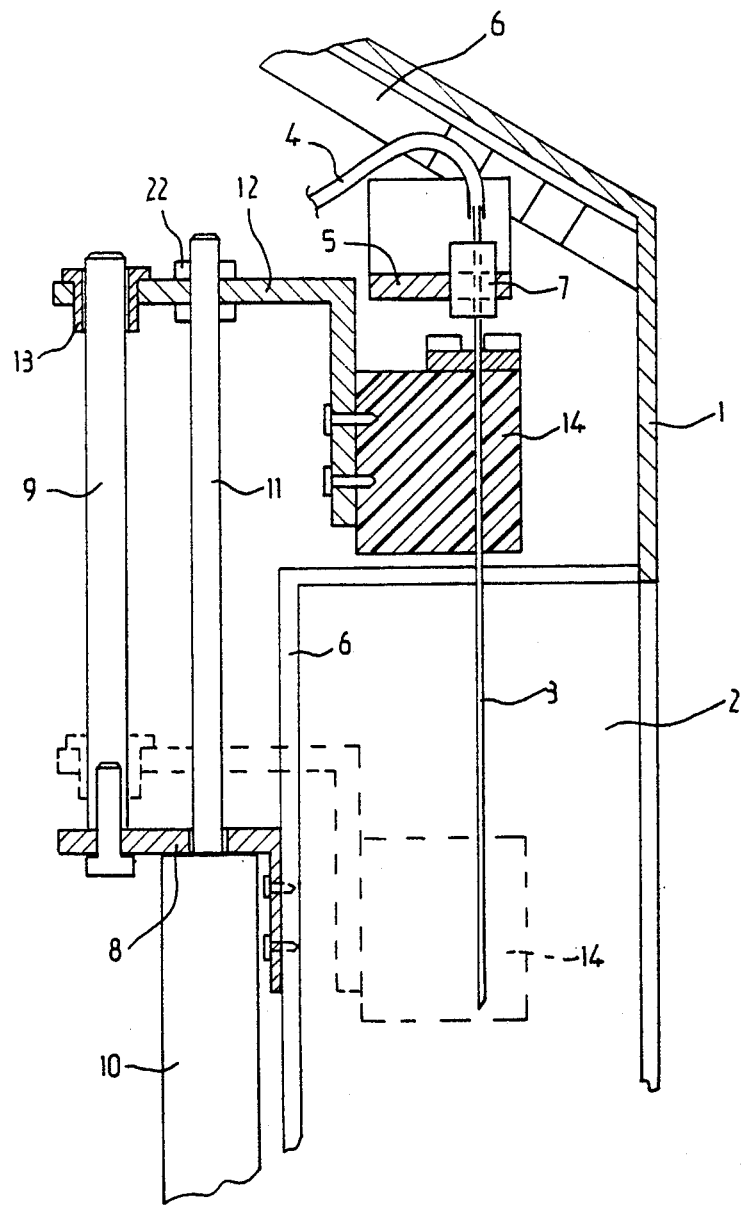

United States Patent [19]

Champseix et al.

[11] Patent Number: 4,817,443

[45] Date of Patent: Apr. 4, 1989

[54] DEVICE FOR CLEANING A LIQUID SAMPLE TAKING NEEDLE

[75] Inventors: Henri Champseix, Montesson; Serge Champseix, Les Mureaux, both of France

[73] Assignee: A.B.X., Levallois Perret-Hauts-de Seine, France

[21] Appl. No.: 119,085

[22] Filed: Nov. 10, 1987

[30] Foreign Application Priority Data

Nov. 14, 1986 [FR] France ................................ 86 15833

[51] Int. Cl.$^4$ ............................ G01N 1/14; B08B 9/02
[52] U.S. Cl. ............................ 73/864.22; 134/169 R; 134/170; 141/91
[58] Field of Search .............. 134/166 R, 169 R, 170, 134/171; 141/90, 91; 422/28, 37; 73/864.22

[56] References Cited

U.S. PATENT DOCUMENTS

| 2,153,105 | 4/1939 | Szecsi | 134/171 X |
|---|---|---|---|
| 3,522,824 | 8/1970 | Allen et al. | 141/90 |
| 3,552,212 | 1/1971 | Ohlin | 141/90 X |
| 3,712,784 | 1/1973 | Siard et al. | 134/166 R X |
| 3,719,086 | 3/1973 | Bannister et al. | 73/864.22 |
| 3,841,160 | 10/1974 | Iwao | 73/864.87 |
| 3,911,749 | 10/1975 | Hendry | 73/864.22 |
| 3,970,426 | 7/1976 | Stark et al. | 422/28 X |
| 4,064,886 | 12/1977 | Heckele | 134/171 X |
| 4,179,932 | 12/1979 | Ranger | 73/864.22 |
| 4,318,885 | 3/1982 | Suzuki et al. | 73/864.22 X |
| 4,342,341 | 8/1982 | Lee | 134/170 X |
| 4,463,615 | 8/1984 | Buzza | 73/864.22 X |

FOREIGN PATENT DOCUMENTS 2354555 1/1978 France .
60-53849 3/1985 Japan .

Primary Examiner—Philip R. Coe
Attorney, Agent, or Firm—Fleit, Jacobson, Cohn & Price

[57] ABSTRACT

A device is provided for cleaning a liquid sample taking needle, mounted fixedly on the frame of a sample taking apparatus, which device includes a mobile mechanism formed of a rinsing case (14) sliding over the sample taking needle (3) between a top position which it occupies during sample taking and a low position which it occupies during cleaning in which it covers the whole of the lower part of the needle, the end of this latter remaining withdrawn inside a cylindrical cleaning chamber (18) provided in the case through which the needle passes and at the lower part of which a depression is applied.

10 Claims, 2 Drawing Sheets

DEVICE FOR CLEANING A LIQUID SAMPLE TAKING NEEDLE

The invention, which relates to the taking of liquid, particularly blood, samples from a flask relates more precisely to a device for cleaning the needle used for taking this liquid sample.

In medical biology analysis laboratories, it is known that automatic apparatus are used for determining a number of parameters such as the number of white blood corpuscles and red blood corpuscles, the dose of hemoglobin etc... from a whole blood sample. The blood samples must then undergo transfers, one at least of which consists in taking a small quantity from a tube by means of a needle which plunges into the blood and sucks up a small volume. After this operation, and before again proceeding with taking a sample, the needle must be carefully rinsed, not only on the inside but also on the outside.

Up to present, it has been usual to dip the needle in a rinsing liquid, this liquid also penetrating inside, then draining it. For the cleaning to be efficient, it was then necessary to dry the needle which complicated the operation and introduced a new cause of pollution. To avoid this drawback and to make sure that cleaning the inside of the needle was correctly carried out, a fixing rinsing block was used. This is a sort of reservoir, in which the mobile needle is dipped further connected by a small flexible tube to a pumping system which causes the rinsing liquid and possible a drying fluid to be sucked into the inside of the needle and driven out. But the depth of the reservoir must then correspond to the length of the needle to be cleaned and said needle must be provided with a sufficiently long connecting tube so as to be able to move in this reservoir, which represents wasted space and a complicated mechanization.

In FR-A-No. 2 354 555 another cleaning device is described fitted to a sample taking pipette which is also movable between a low position in which it plunges into a sample container for taking a sample and a top position in which its end engages inside a washing chamber, a washing solution being injected into this chamber, then sucked into the pipette without flowing through the open lower orifice of the chamber. In this arrangement, the rinsing fluid is sucked inside the pipette in the same direction as the sample is taken. That has the drawback that said rinsing fluid must be recovered from the suction pipe, for feeding it to an associated waste reservoir, which involves the creation of a by-pass circuit on this pipe, with the appropriate routing valve and suction pump.

Another drawback of this device resides in the fact that the air drawn into the pipette with the rinsing fluid forms inside the pipette an emulsion which rinses its inner wall less correctly than its outer wall which is on the contrary cleaned solely by liquid, whereas correct cleaning of the inside of the pipette is more important to obtain than for the outside.

In this case also, the fact of having to move the pipette or the sample taking needle requires a special mechanization to the detriment of the space available.

There exist however systems in which the needle remains in a fixed position. Cleaning of the end of the needle is then provided by mobile rinsing cups which come from underneath so that the needle dips in the liquid which they contain, before being retracted at the end of the rinsing operation. This system involves high accuracy in the movement of the cups with respect to the needle, which makes the operation delicate. All these devices also have the drawback of requiring the use of a not inconsiderable amount of cleaning liquid, to the detriment of speed of operation and cost price.

The invention proposes then a new approach to those problems, overcoming the drawbacks inherent in the known systems, and further having the advantage of being very readily applicable to automatic sample taking apparatus with a fixed needle.

In accordance with the invention, the device for cleaning a liquid sample taking needle, particularly blood samples, mounted on the frame of a sample taking apparatus which uses a mobile mechanism adapted to come into contact with said needle, which mobile mechanism includes a cylindrical cleaning chamber opening outwardly and intended to have the needle passing theretrough, is then formed of a rinsing case sliding over the fixed sample taking needle between a top position in which it frees the lower portion of the needle and leaves it quite accessible for sample taking and a low position which it occupies during cleaning in which it covers the whole of the lower portion of the needle, the end thereof remaining withdrawn inside the cylindrical chamber and in that at the lower portion of said chamber a depression is applied through an orifice which sucks in a rinsing fluid injected from the top inside the needle, which fluid causes inner rinsing counter-currentwise with respect to the direction of taking the liquid sample, a second orifice, in the upper portion of the cylindrical chamber, makes it possible to inject a rinsing fluid for rinsing the outside of the needle.

In accordance with a particular characteristic of the invention, the upper portion of the rinsing case is pierced with a cylindrical chamber through which the needle passes and which is closed by a guide piece, at least one seal, providing sealing with the needle, being disposed at the bottom of the chamber.

In accordance with yet another characteristic of the invention, the rinsing case is fixed to a slide which moves along a fixed guide column parallel to the needle, the mobile rod of a fixed actuating cylinder being fast with the slide and the same bracket fixed to the frame of the sample taking apparatus serving as support for the column and the cylinder.

Other particular features and advantages of the invention will be clear form reading the following description of one embodiment given by way of non limitative example, with reference to the accompanying drawings which show:

FIG. 1 a partial schematical elevational view of the cleaning device, and

Figure 2:
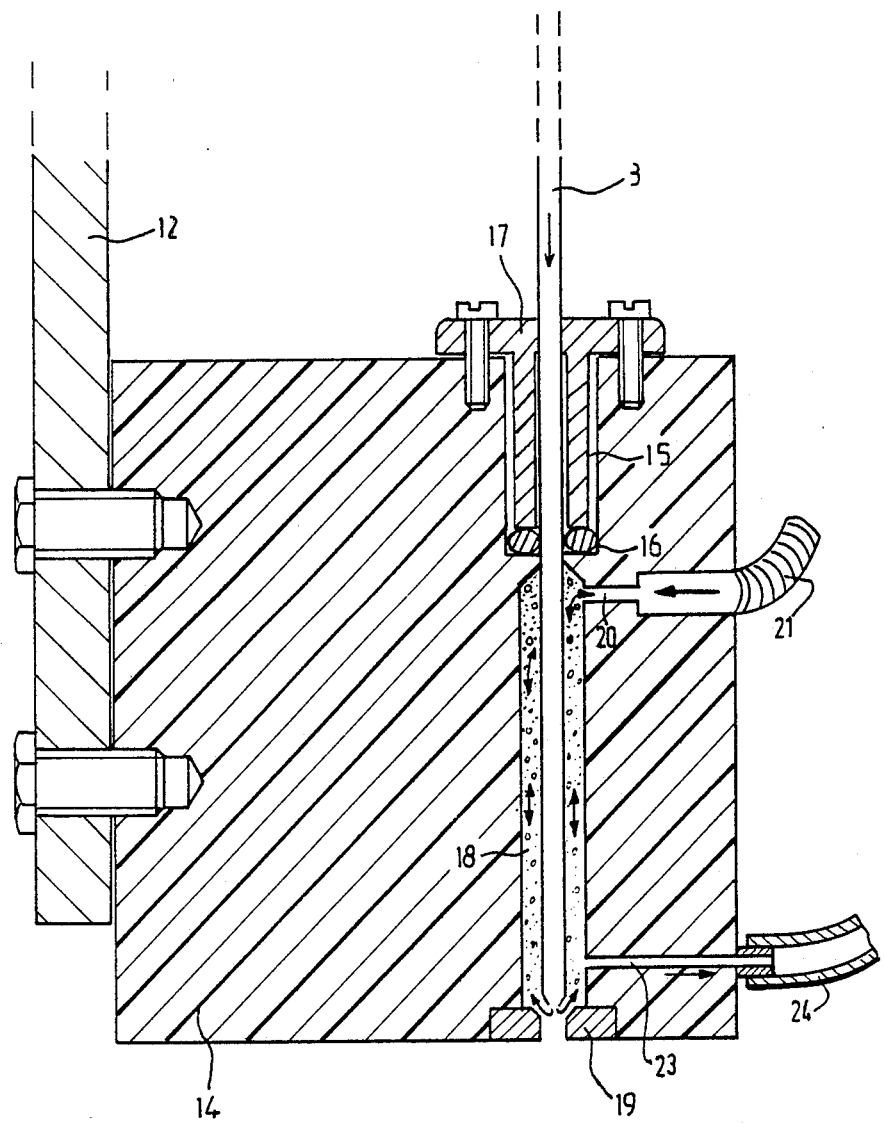

FIG. 2 a sectional enlarged view of the rinsing case.

In FIG. 1 can be seen the front portion 1 of the frame 6 of a sample taking and analysis apparatus, defining a compartment 2 inside which a flask is held in position for a sample taking needle 3 to penetrate inside. The upper end of needle 3, connected to the apparatus by a small flexible pipe 4, is fixed to a bracket 5 secured to frame 6, by means of a floating stirrup 7. This latter supports the needle 3 in a substantially vertical position, as shown, while leaving it a small clearance with respect to its support. On frame 6, in the vicinity of compartment 2, is fixed a right-angled bracket 8 which serves as support for a guide column 9 parallel to needle 3. To this right-angled bracket an actuating cylinder 10 is also fixed, substantially vertically, whose mobile rod 11 also moves parallel to the needle 3. On the guide column 9 is engaged a slide 12 which moves without friction thereover by means of a guide ring 13. The slide is fixed by a clip member 22 at the end of rod 11 of cylinder 10, which ensures its movement from one end to the other of the column. This slide whose end extends inside the sample taking compartment serves for supporting a rinsing or cleaning case 14 which is therefore movable therewith and adapted to move with it from bottom to top and top to bottom by sliding over the sample taking needle 3. The rinsing case shown more precisely in FIG. 2 has therethrough an opening for passing needle 3. At the upper portion is formed a cylindrical chamber 15 through which the needle 3 passes and at the bottom of which are provided two 0 seals 16. A guide piece 17 is further fixed to the top of chamber 15 for guiding the needle 3 and compressing the seal. At the lower portion is provided a cylindrical cleaning chamber 18 whose lower part is open outwardly, the opening being bordered by a profiled end piece 19. The base of this chamber communicates through an orifice 23 with a suction duct 24 itself connected to a pump not shown.

The top of chamber 18 also communicates through an additional orifice 20 with an injection pipe 21 also connected to a pump not shown, this pipe only introducing fluid at the top of chamber 18, in the direction shown by the arrow, contrary to pipe 24 which only sucks fluid from the low part of said chamber.

FIG. 1 shows the rinsing case 14 held in the top position by the extended rod 11 of the cylinder. The needle 3 part situated in compartment 2 is therefore quite accessible to the user who can present thereto a flask for taking a sample. When the blood has been taken through pipe 4, cylinder 10 is actuated in the direction for retracting rod 11 and lowering slide 12. The rinsing case 14 then moves down, during which movement rinsing fluid is injected through pipe 21 into the upper part of chamber 18 at the level of orifice 20 and simultaneously suction is provided in pipe 24 which creates a depression at the base of chamber 18 through orifice 23. Consequently, during the downward movement of the rinsing case in a manner of speaking a first cleaning of the outside of the needle 3 takes place over the whole of its height which avoids saturation of blood in the device and the rinsing circuits.

Then the rinsing case 14 reaches the low position shown in FIG. 2 and with dotted lines in FIG. 1, in which position it encloses the whole of the lower part of needle 3. The lower end of needle 3 is then slightly withdrawn inside the lower orifice of the case, inside chamber 18. As soon as this low position is reached, the injection of fluid through pipe 21 is interrupted, by suction is maintained through pipe 24 and simultaneously rinsing fluid is injected, but from the top through pipe 4 and consequently inside needle 3 and in counter flow to the blood sample taking direction. Because of this injection from the top, the fluid will rinse the inside of needle 3 over the whole of its height then emerge at the low part in the vicinity of end piece 19. It will then be sucked through orifice 23 and thus the fluid will not flow outside case 14. The position and shape of the profiled end piece 19 are adapted for cooperating with the lower end of needle 3 so as to avoid the flow of rinsing fluid outside the case. After this operation, case 14 rises to the top position.

During this rinsing operation, the injection of fluid is interrupted through pipe 4 but, on the other hand, it is re-established through pipe 21 and since suction through pipe 24 is maintained, complementary safety cleaning of the end portion of the needle 3 is provided during this phase.

The apparatus is ready for taking a new sample.

This device makes possible then cleaning of needle 3 even of a great length both inside and outside, by means of a simplified rinsing case. Its size is reduced and it readily retracts to the top of the apparatus during sample taking. The volume of rinsing fluid is very much reduced as well as the volume sucked in by pipe 24; furthermore, no liquid can spread over the bottom of the apparatus although chamber 18 is not closed at its lower part.

Inner cleaning of the needle 3 in counter flow to the direction of sample taking, combined with external cleaning, through complementary injection of fluid through pipe 21, and external cleaning of the upper part of the needle 3 by seals 16 gives much better results than with known devices.

In an advantageous embodiment, needle 3 is slanted with respect to the vertical which makes the introduction of the sample flask and its handling easier. In addition, with needle 3 fixed to its support 5 by the floating stirrup 7, it is not rigidly held in position and may assume certain slight slants with respect to its original position during sliding of case 14, which avoids any risk of jamming. With the case support perfectly guided by column 9 and ring 13, a small sized and small powered cylinder 10 is sufficient for moving the case. Similarly, this latter may readily slide over needle 3 because of the guide piece 17 which slides without friction on the outer wall of the needle

We claim:

1. A device for cleaning a sample taking needle, particularly a blood sample, comprising a frame, a needle for taking samples mounted on the frame, a mobile means mounted on said frame for contacting with said needle, said mobile means having a cylindrical cleaning chamber opening outwards with the needle received in the cleaning chamber, said mobile means being slidable over the needle between a high position at which the lower part of the needle projects out of the mobile means and is accessible for taking a liquid sample and a low position at which the mobile means covers the whole of the lower part of the needle, with the end of the needle lying withdrawn inside the cylindrical chamber, and fluid cleaning means for applying a vacuum at the lower part of said chamber for sucking a rinsing fluid injected through the needle for providing inner rinsing in a counterflow with respect to the liquid sample taking direction.

2. A device as in claim 1, wherein said mobile means comprises a guide means for guiding said needle into said cylindrical chamber.

3. A device as in claim 2, wherein said mobile means further comprises at least one seal for sealing the needle therein.

4. A device as in claim 1, wherein the mobile means has an inlet located at the upper part of the chamber for injection of fluid to externally clean the needle.

5. A device as in claim 1, wherein the mobile means comprises a profiled end piece to cooperate with the lower end of the needle to inhibit rinsing fluid from flowing through the outward opening of the chamber.

6. A device as in claim 1, wherein the frame comprises a fixed guide and said mobile means is guided by said fixed guide parallel to the needle.

7. A device as in claim 6, wherein the mobile means comprises a slide mounted on said fixed guide for relative sliding movement.

8. A device as in claim 6, wherein a rod and a cylinder assembly is mounted on the frame, one of said rod and said cylinder connected to the frame and the other connected to said mobile means.

9. A device as in claim 8, wherein said frame comprises a right-angled bracket, said right-angle bracket supporting both the fixed guide and the cylinder.

10. A device as in claim 1, wherein said frame comprises a floating stirrup to support the needle in a substantially vertical position.

* * * * *